United States Patent [19]

Samuels et al.

[11] Patent Number: 5,290,517
[45] Date of Patent: Mar. 1, 1994

[54] OPTICAL AGGLUTINATION ASSAY DEVICE

[75] Inventors: Brian C. Samuels, Pasadina; Jeffry A. Reidler, Frederick, both of Md.; David B. Silcott, Kamas, Utah

[73] Assignee: Westinghouse Electric Corp., Pittsburgh, Pa.

[21] Appl. No.: 503,623

[22] Filed: Apr. 4, 1990

[51] Int. Cl.⁵ .............................................. G01N 21/59
[52] U.S. Cl. .................................. 422/58; 422/81; 422/82.09; 422/93; 422/100; 356/338
[58] Field of Search .................. 422/58, 57, 81, 82.05, 422/100, 93, 82.09; 436/165, 164, 43, 53; 435/301; 356/246, 336, 338

[56] References Cited

U.S. PATENT DOCUMENTS

| | | | |
|---|---|---|---|
| 3,802,786 | 4/1974 | Anderson et al. | 356/246 |
| 4,452,902 | 6/1984 | Suovaniemi et al. | 436/805 |
| 4,551,308 | 11/1985 | Mintz | 422/58 |
| 4,585,623 | 4/1986 | Chandler | 422/58 |
| 4,597,944 | 7/1986 | Cottingham | 422/73 |
| 4,769,216 | 9/1988 | Chandler et al. | 422/58 |
| 4,775,515 | 10/1988 | Cottingham | 422/58 X |
| 4,806,015 | 2/1989 | Cottingham | 422/73 X |
| 4,829,011 | 5/1989 | Gibbons | 436/520 |
| 4,963,498 | 10/1990 | Hillman et al. | 422/73 |
| 4,999,286 | 3/1991 | Gawel et al. | 436/518 |
| 5,053,197 | 10/1991 | Bowen | 422/82.09 X |

Primary Examiner—James C. Housel
Assistant Examiner—Jeffrey R. Snay
Attorney, Agent, or Firm—Norman A. Nixon

[57] ABSTRACT

An optical agglutination assay device for detecting cocaine. The device includes a hollow reaction cell defining a generally planar liquid receiving reaction chamber having a thickness which is insufficient to diminish the intensity of a ray of light passing through an aqueous reaction system in the chamber in a first direction transversely of the plane of the latter. The device also includes a pusher assembly for delivering an aqueous agglutination reaction system and an unknown substance suspected of containing cocaine into the chamber. The agglutination system is such that agglutination is inhibited in the presence of cocaine. The device also includes an optical transmitting and receiving unit aligned with the reaction cell for measuring the intensity of light reflected from the chamber as a measure of the occurrence of agglutination in the reaction system.

17 Claims, 13 Drawing Sheets

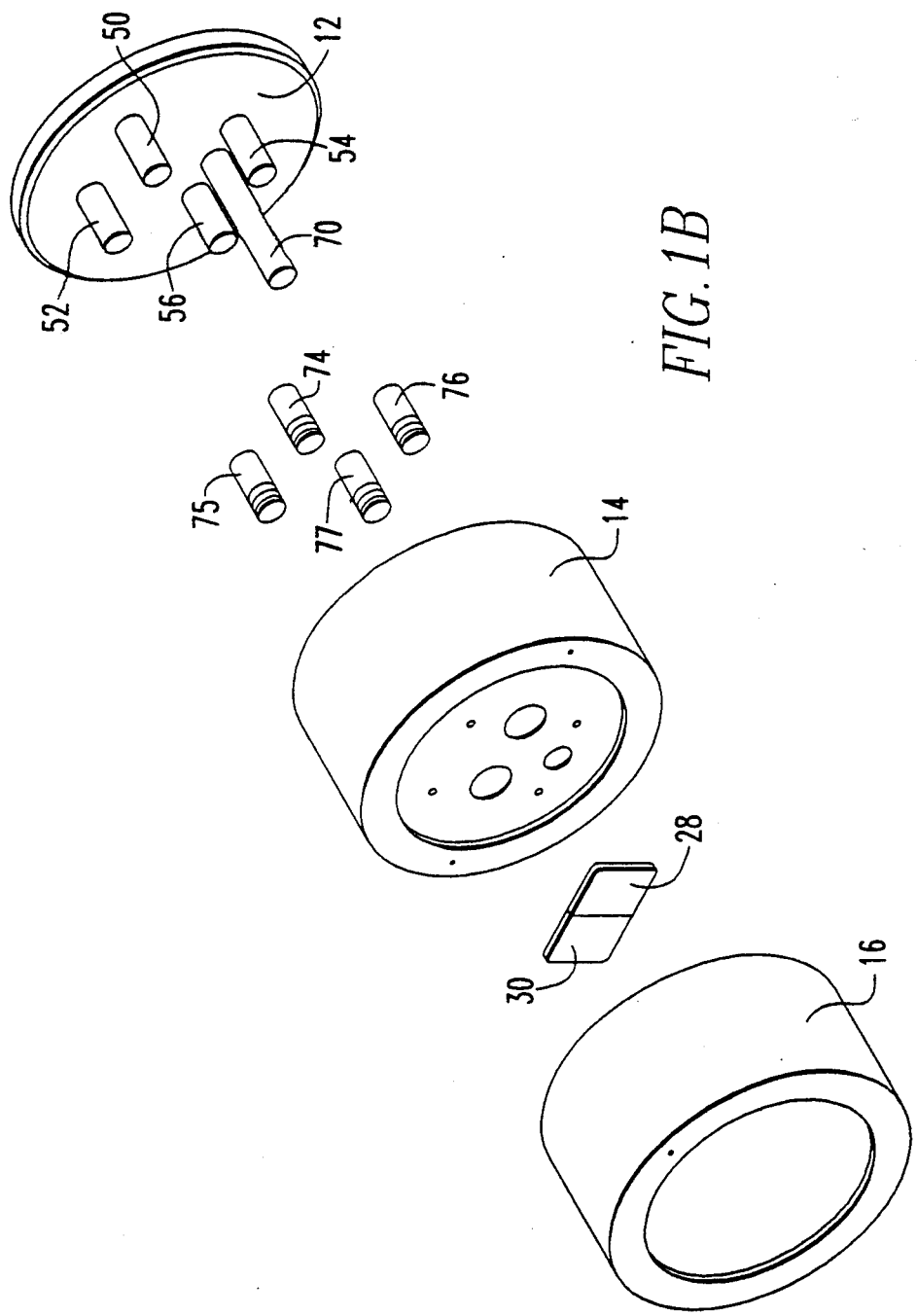

OPTICAL AGGLUTINATION ASSAY DEVICE

BACKGROUND OF THE INVENTION

1. Field of the Invention

The present invention relates to devices and methodology for detecting the presence of analytes. In particular the invention relates to such devices and methodology whereby assays may be quickly and efficiently conducted in the field using an optical reading instrument.

2. The Prior Art Scenario

There is a present and continuing need to detect a wide variety of analytes with high specificity and high sensitivity in many applications. A technique that has developed over the past 30 or more years is the use of antibody/antigen reactions to provide high specificity and sensitivity and to develop an assaying technique using the antibody/antigens to provide metering or quantitation of the concentration of the requested analyte. One common use of the antibody/antigen pair is in the construction of a reaction environment in which microscopic particles to which antibody or antigens have been chemically attached are made to agglutinate or are inhibited from agglutinating in the presence of the mating antibody/antigen and the target analyte. When an agglutination reaction occurs the microscopic particles chemically bind to each other, with the antibody/antigen molecules serving as very specific chemical binding agents, forming much larger aggregates of particles which can grow in size to become easily visible to the naked eye. The progress of the reaction may be monitored and resulting data analyzed to provide quantitative results on target analyte concentration.

One approach to monitoring the agglutination reaction is to illuminate the sample with light of some frequency band or many frequency bands and to use the interaction of the light with the reacting material to extract qualitative and/or quantitative information about the analyte(s) in question. Many such approaches have been described and they rely on a variety of properties of light interaction including light transmittance (U.S. Pat. No. 4,205,954), light scattering (Leonard T. Greenburg, *Clinical Chemistry*, Vol. 21, No. 9, 1975, pp. 1234–1237; U.S. Pat. No. 4,174,952 and the Periodical Molecular Immunology Vol. 17, 1980, pp. 81–92), Doppler shift spectrum broadening and light beating spectroscopy (U.S. Pat. No. 4,080,264; U.S. Pat. No. 4,446,239 and the periodical *Immunochemistry*, Vol. 12, 1975, pp. 349–351 and Vol. 13, 1976, pp. 955–962). Each of these approaches involves the use of complex and expensive equipment and would be very difficult to package into a portable instrument.

The method with the greatest potential for incorporation into a low cost apparatus is that described in U.S. Pat. No. 4,205,954 by Babson. However, this approach relies on a change in the transmittance of a sample during an agglutination reaction and requires that the sample be under constant agitation to achieve consistent and reliable measurements. In addition all of the approaches cited above do not describe a simple one-step user-friendly device for the collection and subsequent reaction of the unknown analyte with the requisite reagents.

SUMMARY OF THE INVENTION

We have discovered that by using a light source/detector pair designed to illuminate and collect reflected light from an appropriately designed reaction cell in which an antibody/antigen agglutination reaction has been initiated one may by analyzing the signal generated by the photodetector determine either qualitative or quantitative information about the concentration of specific analyte(s) which are present in the reaction mixture undergoing agglutination. Because the technique uses antibody/antigen interaction the reactions are specific and sensitive. Thus this approach becomes a generic one for the detection of any analytes for which an antigen/antibody pair can be made. In addition because of the unique design of the reaction cell and light source/detector the apparatus can be easily configured into a hand held portable unit with a low cost disposable reaction cell/sample collector assembly.

An object of this invention is to provide a method and approach for the detection and measurement of an analyte in a sample or on a surface.

A further object is to provide an apparatus that houses a sample collection device, all necessary reagents and the requisite reaction cells in a low cost disposable unit that provides for a simple one step collection-reaction initiation by the user.

A further object is to provide a reusable photometric reaction cell reading device which will mate with the unique collection apparatus and provide a qualitative or quantitative determination of the analyte(s) concentration in the test sample.

In accordance with the invention, the invention provides an optical agglutination assay device. The device comprises a hollow reaction cell defining a generally planar liquid receiving reaction chamber having a thickness which facilitates the use of small quantities of reactants, does not interfere with the agglutinating process and is insufficient to substantially interfere with the passage of light through an aqueous reaction system in said chamber in a first direction transversely of the plane of the latter. The device also includes means for delivering an aqueous agglutination reaction system and an unknown substance suspected of containing a target analyte into the chamber. The agglutination system is such that agglutination therein is promoted or inhibited in the presence of an analyte. The device also includes means for transmitting light into the chamber in the first direction and means for detecting the intensity of the light reflected from the chamber in a direction opposite to the first direction as a measure of occurrence of agglutination in the system.

In a more specific aspect of the invention, the device includes a housing which carries the cell and the agglutination reaction system delivering means. The delivering means comprises an elongated passageway extending through the housing and arranged in liquid communication with the chamber of the cell. The delivering means also includes an elongated plunger in the passageway for pushing components of a reaction system along the passageway into the chamber. The delivery means further comprises an elongated sample duct extending through the housing arranged in liquid communication with the passageway and the chamber. An elongated sample collector is positioned in the duct and configured to extend therethrough for positioning a sample in proximity to the chamber.

Preferably the duct has an internal end and the passageway includes an internal conduit which communicates with the internal end of the duct and with the chamber. The conduit is arranged so that reaction system components pushed by the plunger flow past the internal end of the duct before entering the chamber. Ideally the sample collector has a distal end element operable for carrying a sample and positioning the sample in fluid flowing through the conduit.

In the preferred mode of the invention, the passageway and the duct are disposed to extend in parallelism through the housing and the delivering means includes a pusher member which carries the plunger and the collector with the plunger and the collector mounted to extend in parallelism in positions to be respectively and simultaneously received in the passageway and the duct so that the plunger pushes the components at the same time that the collector positions the sample in the flowing fluids.

When the reaction system initially comprises two separate liquid mixtures, the delivering means may comprise two of the elongated passageways extending through the housing and two of the elongated plunger. In this form of the invention, both plungers and the sample collector extend in parallelism from the pusher member.

In another aspect of the invention, the device may comprises first and second hollow reaction cells as defined above. Preferably the cells are disposed in side-by-side relationship with the chambers disposed in essentially the same plane. One of these cells may be used as a control for establishing a background against which the cell which receives the analyte can be compared. Once again the delivering system includes a number of parallel members which are actuated simultaneously to push the reacting system components into the cells and contact the fluid moving into the test cell with an analyte containing sample.

In a particularly preferred form of the invention, switch and timing means are coupled with the pusher member energizing the intensity detecting or comparing means only after a preset incubation period has elapsed.

DESCRIPTION OF THE DRAWINGS

FIG. 1B is an exploded perspective view of the device of FIG. 1 taken from another angle;

DETAILED DESCRIPTION OF THE PREFERRED EMBODIMENTS

Figure 1:
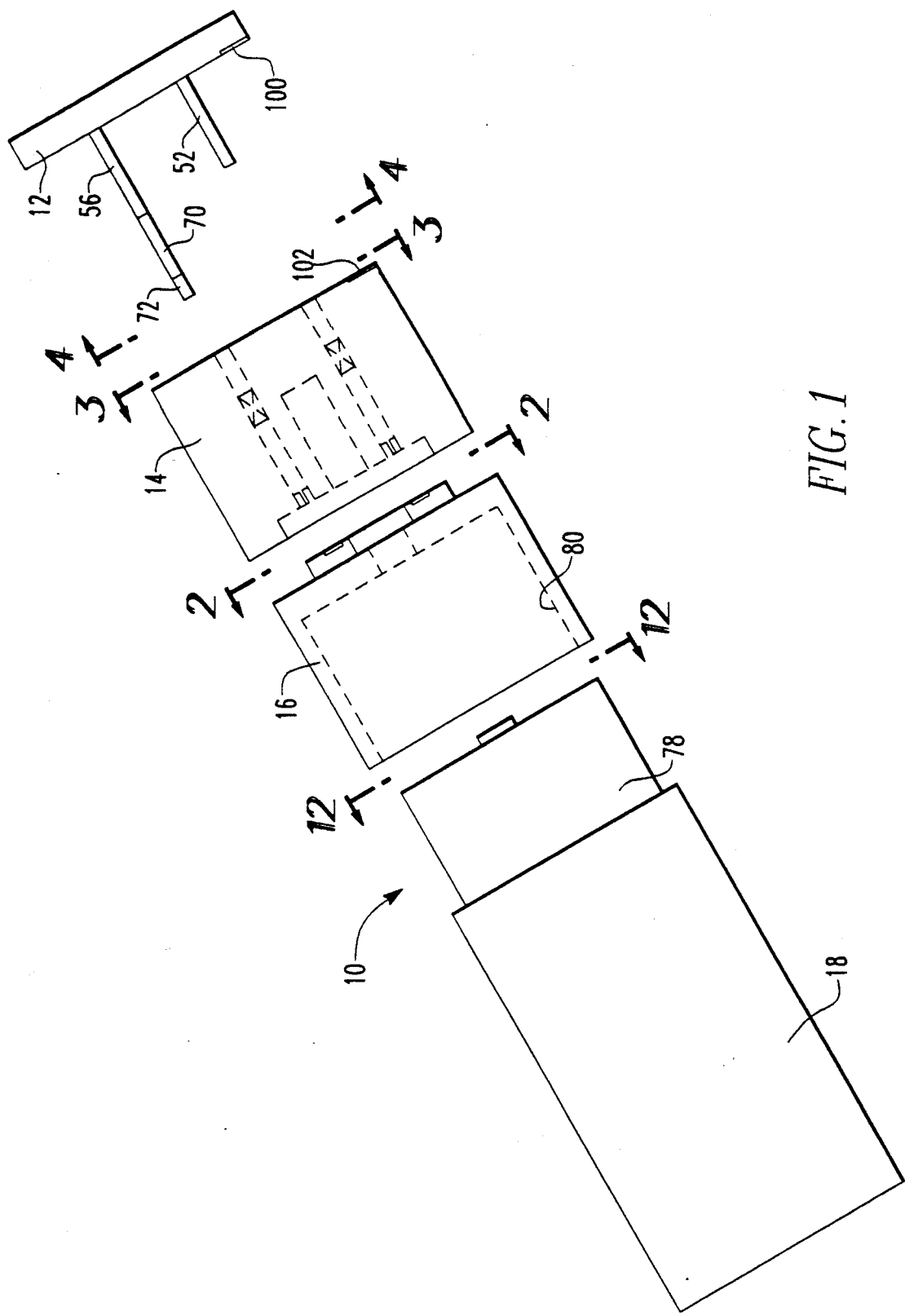
FIG. 1 is an exploded side elevational view of the entire device which embodies the concepts and principles of the present invention.
Figure 12:
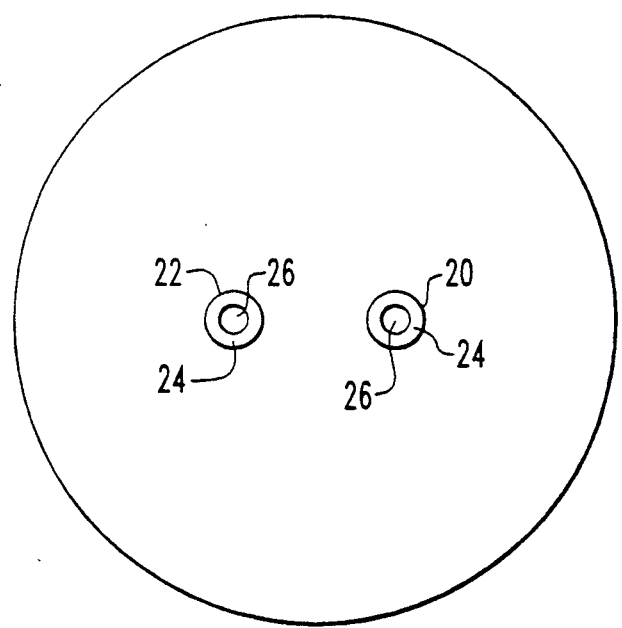
FIG. 12 is a plan view taken along line the 12—12 of FIG. 1.

An assay device 10 which embodies the principles and concepts of the present invention is illustrated in FIG. 1. Device 10 includes a pusher assembly 12, an upper housing member 14, a lower housing member 16 and an optical transmitting and receiving assembly 18. As can be seen in FIG. 12, assembly 18 includes two optical transmitting and receiving units 20 and 22 which for all practical purposes are identical and essentially the same as the optical device illustrated and described in U.S. Pat. No. 4,868,767. In this regard, each of the units 20 and 22 includes an optical transmitter 24 and an optical receiver 26.

Figure 2:
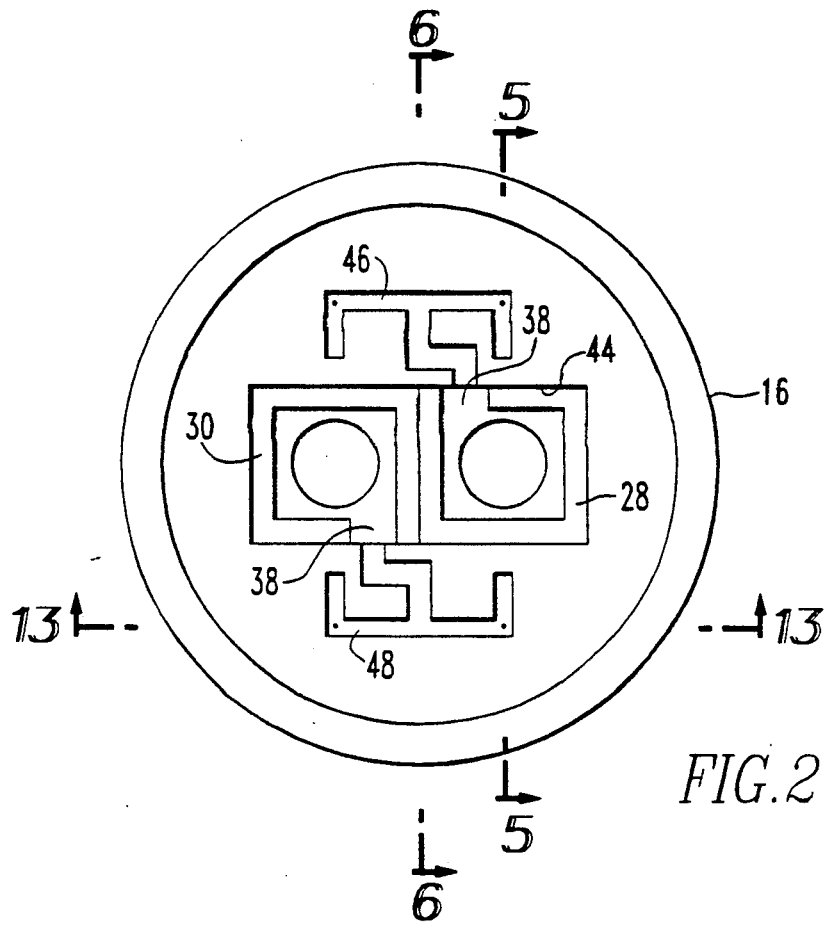
FIG. 2 is a plan view taken along the line 2—2 of FIG. 1.
Figure 7:
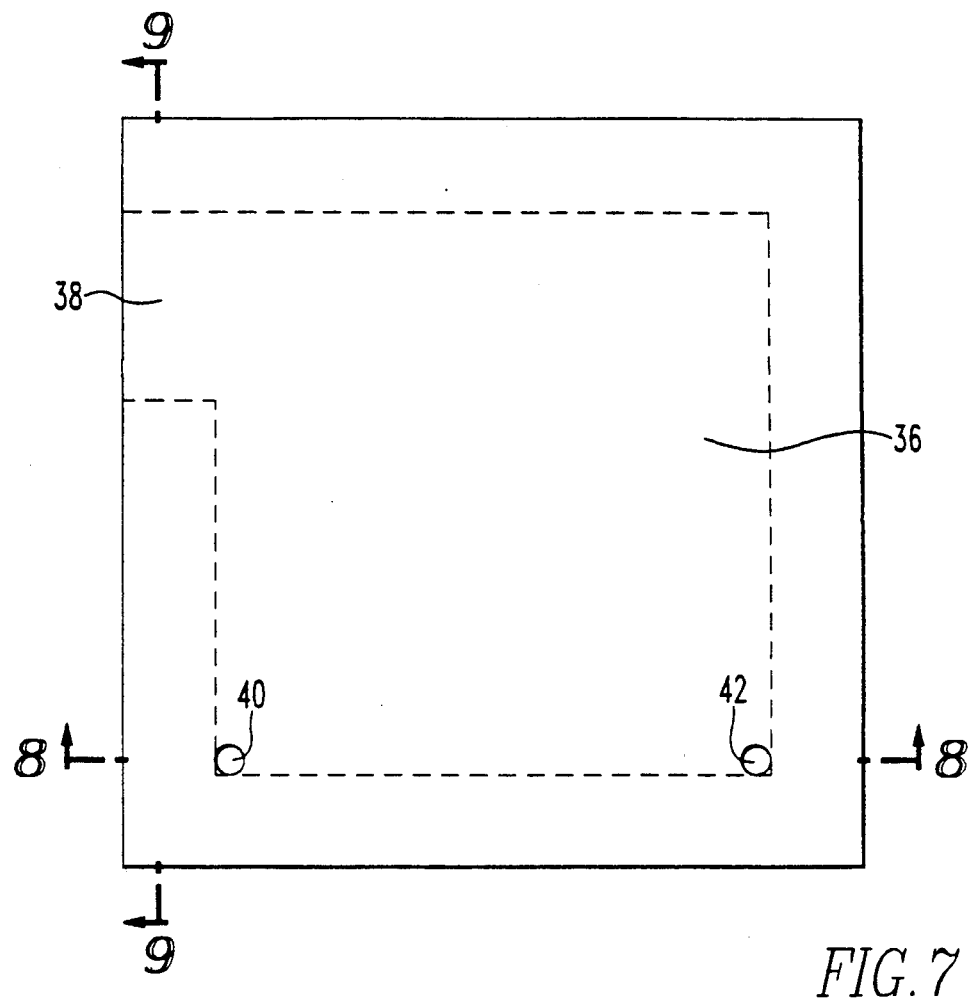
FIG. 7 is a plan view of a reaction cell utilized in the device of FIG. 1.
Figure 8:
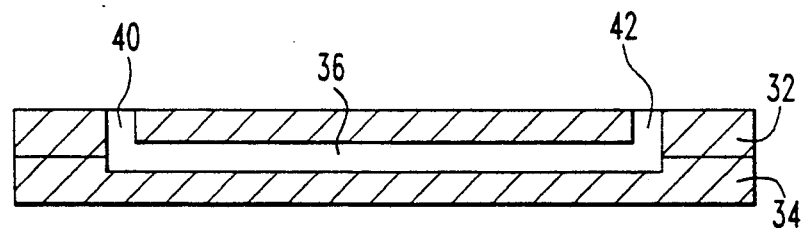
FIG. 8 is a cross-sectional view taken along the line 8—8 of FIG. 1.
Figure 9:
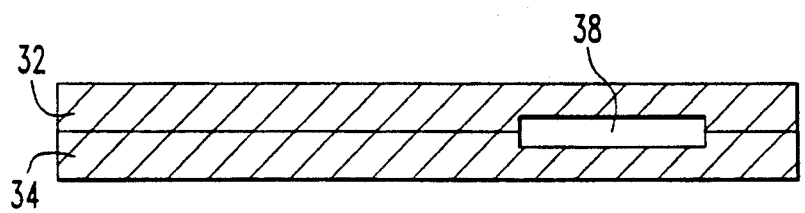
FIG. 9 is a cross-sectional view taken along the line 9—9 of FIG. 7.

Lower housing member 16 is configured to carry a pair of agglutination reaction cells 28 and 30 disposed in side-by-side relationship as illustrated in FIG. 2. The individual cells are illustrated in FIGS. 7, 8 and 9 where it can be seen that each cell 28 (or 30) consists of an upper layer 32 and a lower layer 34. The layers 32 and 34 are configured to present a liquid receiving chamber 36 therebetween. The upper and lower layers also define an inlet 38 for chamber 36 and a pair of vent holes 40 and 42 are provided to facilitate filling of the chamber with reaction fluid during the conduct of an assay.

Chamber 36 has a thickness which facilitates the use of small quantities of reactants, does not interfere with the agglutination process and is insufficient to substantially interfere with the passage of light through an aqueous reaction system contained therein. The thickness of chamber 36 may be within the range of from less than about 1 mil to greater than about 50 mil. In the preferred form of the invention illustrated in the drawings, chamber 36 has a thickness of approximately 10 mil; however, the thickness may be determined empirically and should simply be insufficient to interfere with the optical procedures. Moreover, since the reaction in accordance with the preferred embodiment of the present invention involves agglutination, the chamber 36 must have sufficient thickness so that it does not mechanically interfere with the development and movement of the agglutinate. In any event, the chamber 36 is so thin that it may be defined as being essentially planar. The chamber 36 is thus a planar liquid receiving chamber and the cells 28 and 30 may be characterized as being hollow reaction cells.

With reference once again to FIG. 2, cells 28 and 30 are coplanarly received in an appropriate cavity 44 in lower housing member 16. The cavity 44 may particularly be seen with reference to FIGS. 5 and 6. Cells 28 and 30 are disposed in cavity 44 with their inlets 38 disposed in liquid communication with a respective conduit 46 or 48. The conduits have a configuration essentially as illustrated in FIG. 2 and the same have a depth sufficient to provide a capillary flow path for liquid reaction medium flowing toward cells 28 or 30 as the case may be.

Figure 5:
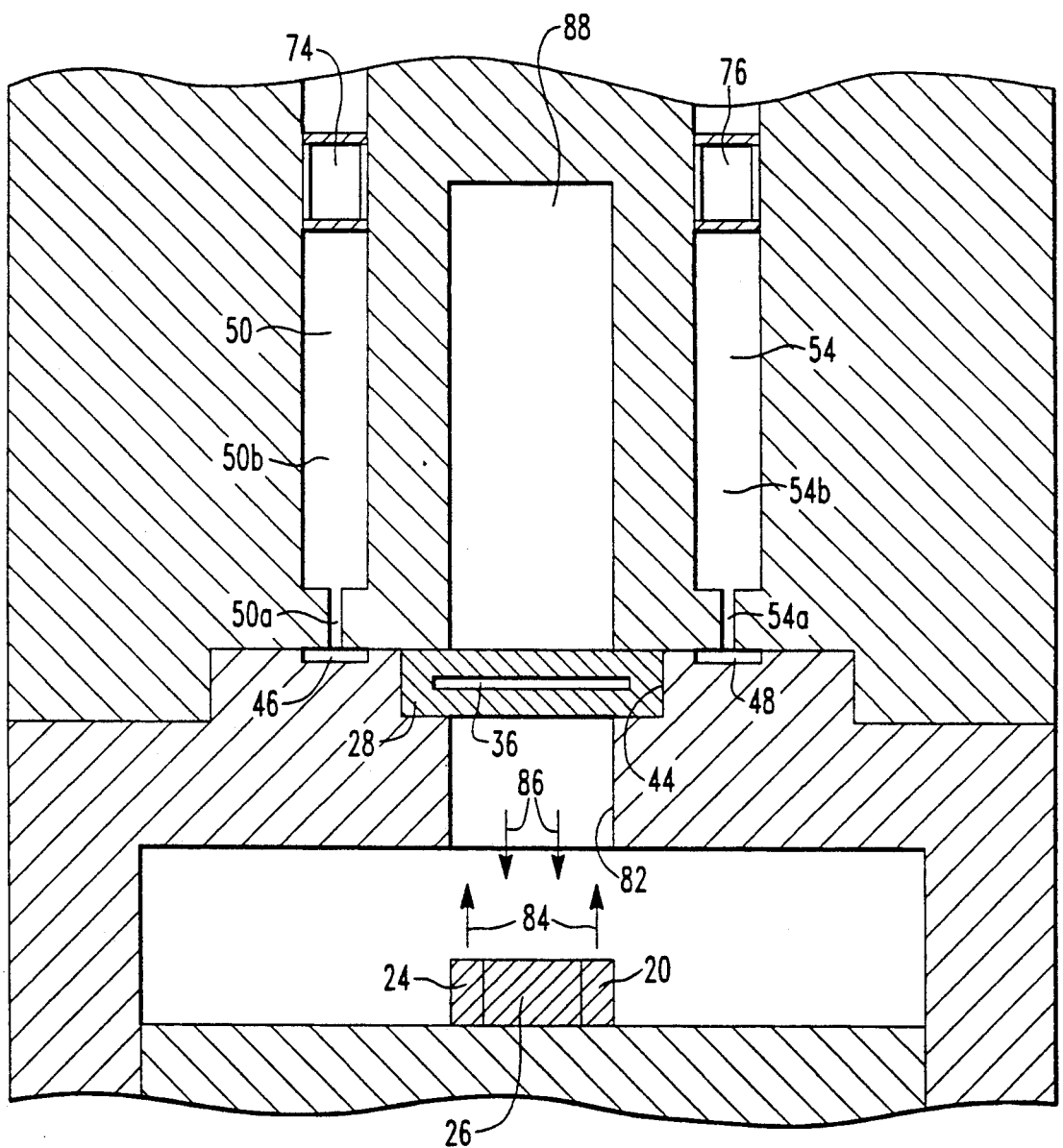
FIG. 5 is a cross-sectional view taken along the line 5—5 of FIG. 2.
Figure 6:
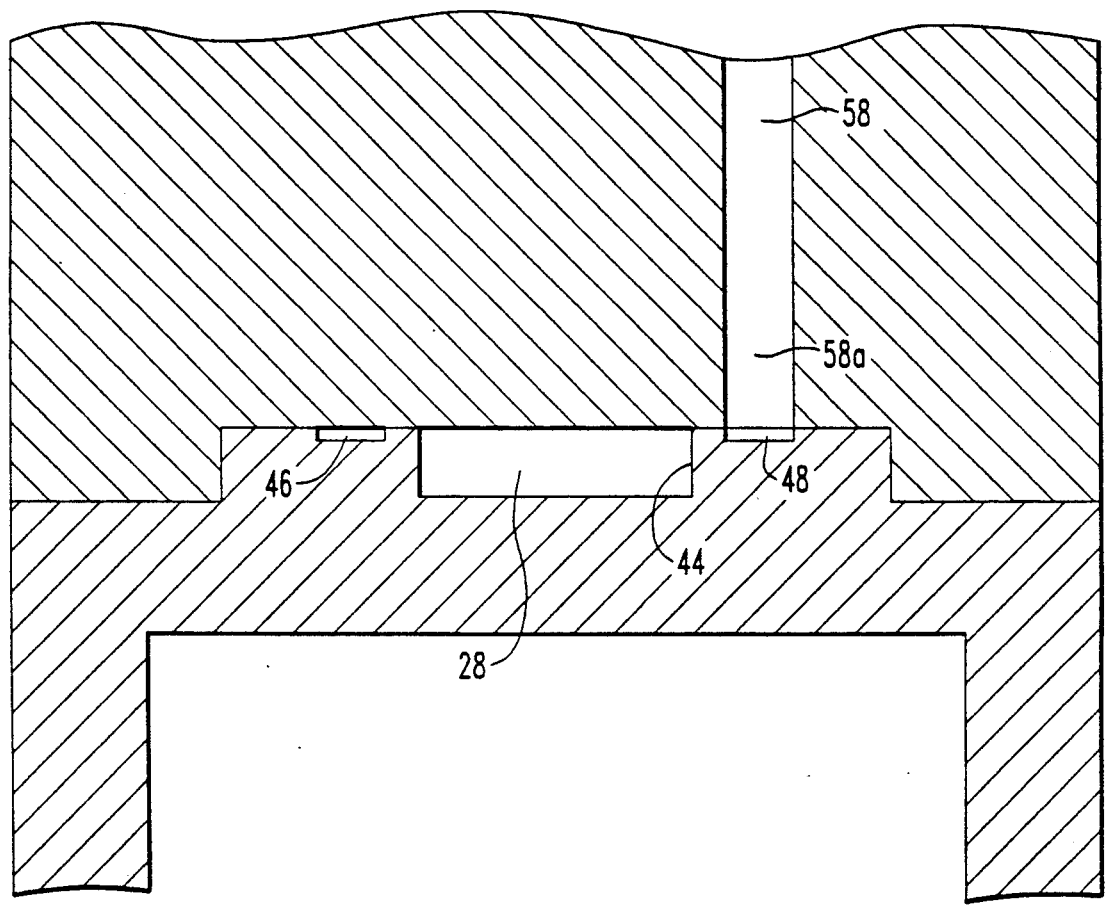
FIG. 6 is a cross-sectional view taken along the line 6—6 of FIG. 2.
Figure 13:
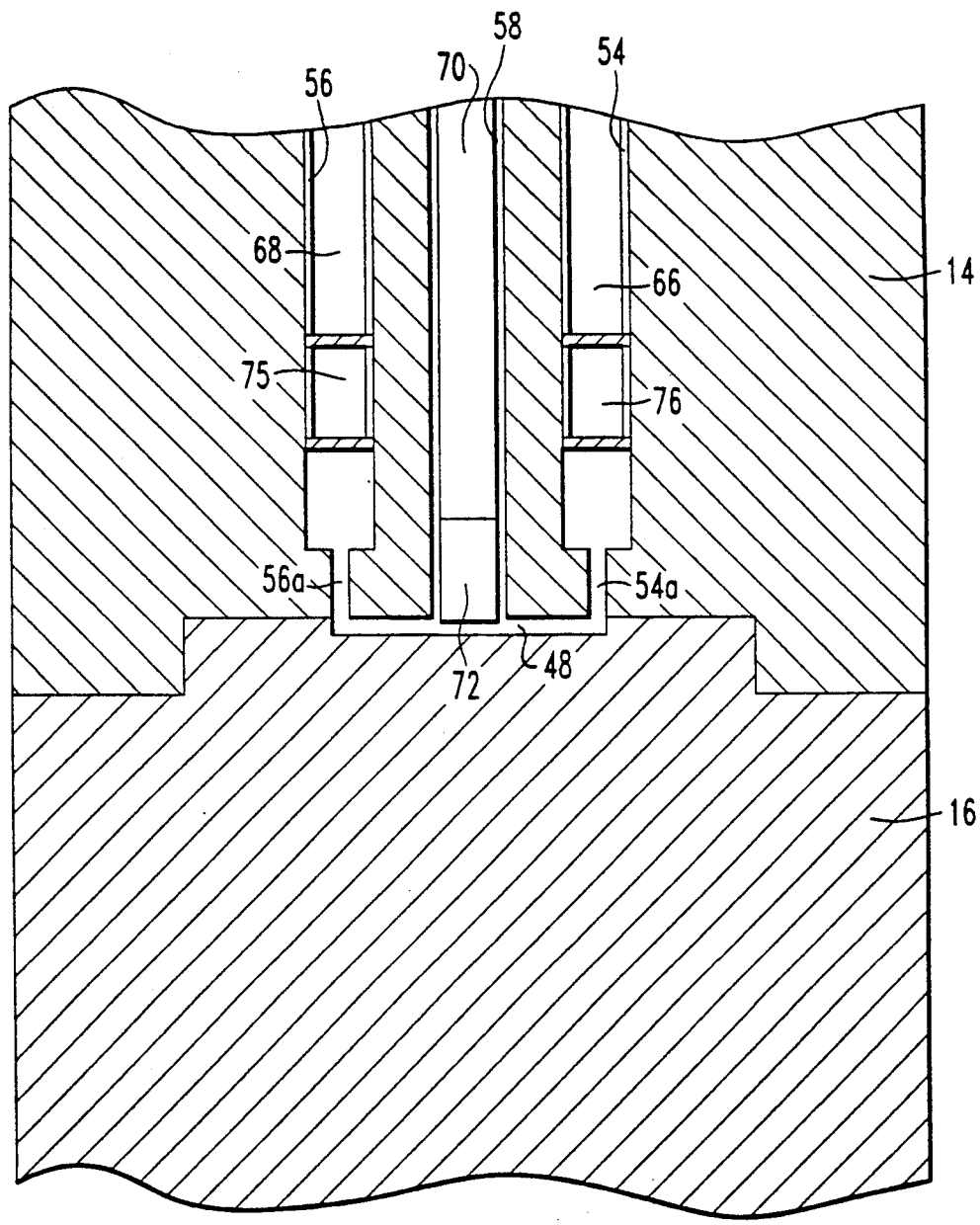
FIG. 13 is a cross-sectional view taken along the lines 13—13 of FIG. 2.

Upper housing member 14 is illustrated in FIGS. 3, 5, 6 and 13. In this regard, FIGS. 5, 6 and 13 are described as being cross-sectional views taken along lines 5—5, 6—6 and 13—13 of FIG. 2; however, the actual FIGS. 5, 6 and 13 also include pertinent views of upper housing member 14 taken along the same plane.

Figure 3:
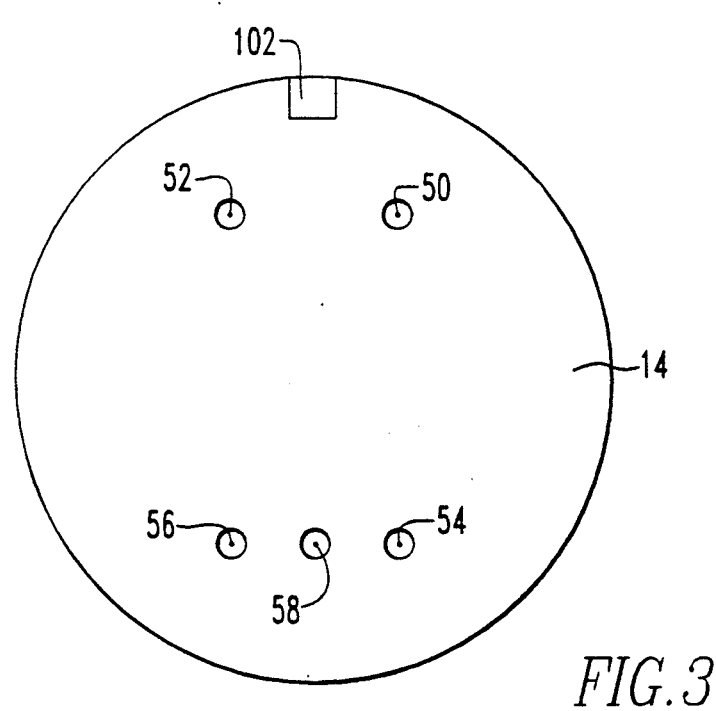
FIG. 3 is a plan view taken essentially along the line 3—3 of FIG. 1.

With reference to FIG. 3, housing member 14 is provided with four elongated passageways 50, 52, 54 and 56 which extend through housing member 14. Each passageway has a capillary opening 50a, 52a, 54a or 56a at the lower end thereof which, as illustrated in FIG. 5, is in fluid communication with the corresponding conduit 46 or 48. Thus, each of the passageways, 50, 52, 54 and 56 has its lower end in fluid communication with the corresponding conduit.

Housing member 14 is also provided with a duct 58 which extends through housing member 14. And as can be seen in FIG. 6, the lower end 58a of duct 58 is aligned with conduit 48 and is in fluid communication therewith. Since conduit 48 is in fluid communication with passageways 54 and 56 and also with cell 30, duct 58 likewise is in fluid communication with passageways 54 and 56 and chamber 36 of cell 30. Clearly, it can be seen from the drawings that passageways 50, 52, 54 and 56 and duct 58 are all arranged to extend in parallelism relative to one another through housing member 14.

Figure 4:
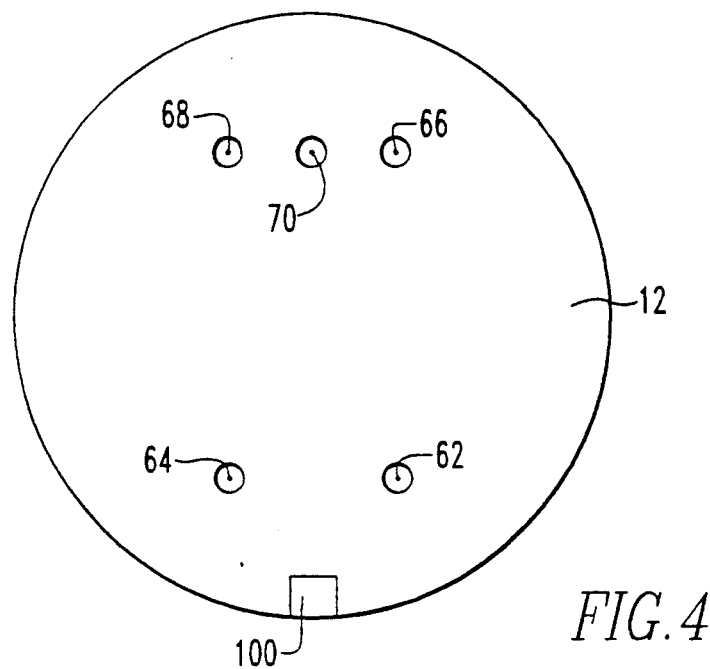
FIG. 4 is a plan view taken along the line 4—4 of FIG. 1.
Figure 10:
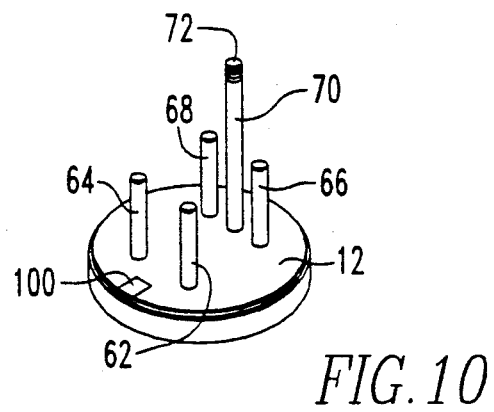
FIG. 10 is a perspective view of the assembly of FIG. 4.

Pusher member 12 for device 10 is illustrated in FIGS. 1, 4 and 10. Pusher member 12 includes a series of elongated plungers 62, 64, 66 and 68 and a sample collector 70. Sample collector 70 has a distal end element 72. And as can be seen viewing FIG. 10, plungers 62, 64, 66 and 68 and sample collector 70 are all carried by pusher member 12 so that the same are disposed in essential parallelism. Moreover, the plungers 62 through 68 and sample collector 70 are positioned on pusher member 12 such that plunger 62 may be aligned with passageway 50, plunger 64 may be aligned with passageway 52, plunger 66 may be aligned with passageway 54 and plunger 68 may be aligned with passageway 56. At the same time sample collector 70 will be in alignment with duct 58 so that these elements may all be pushed simultaneously into their corresponding and respective passageways and/or duct.

Figure 1A:
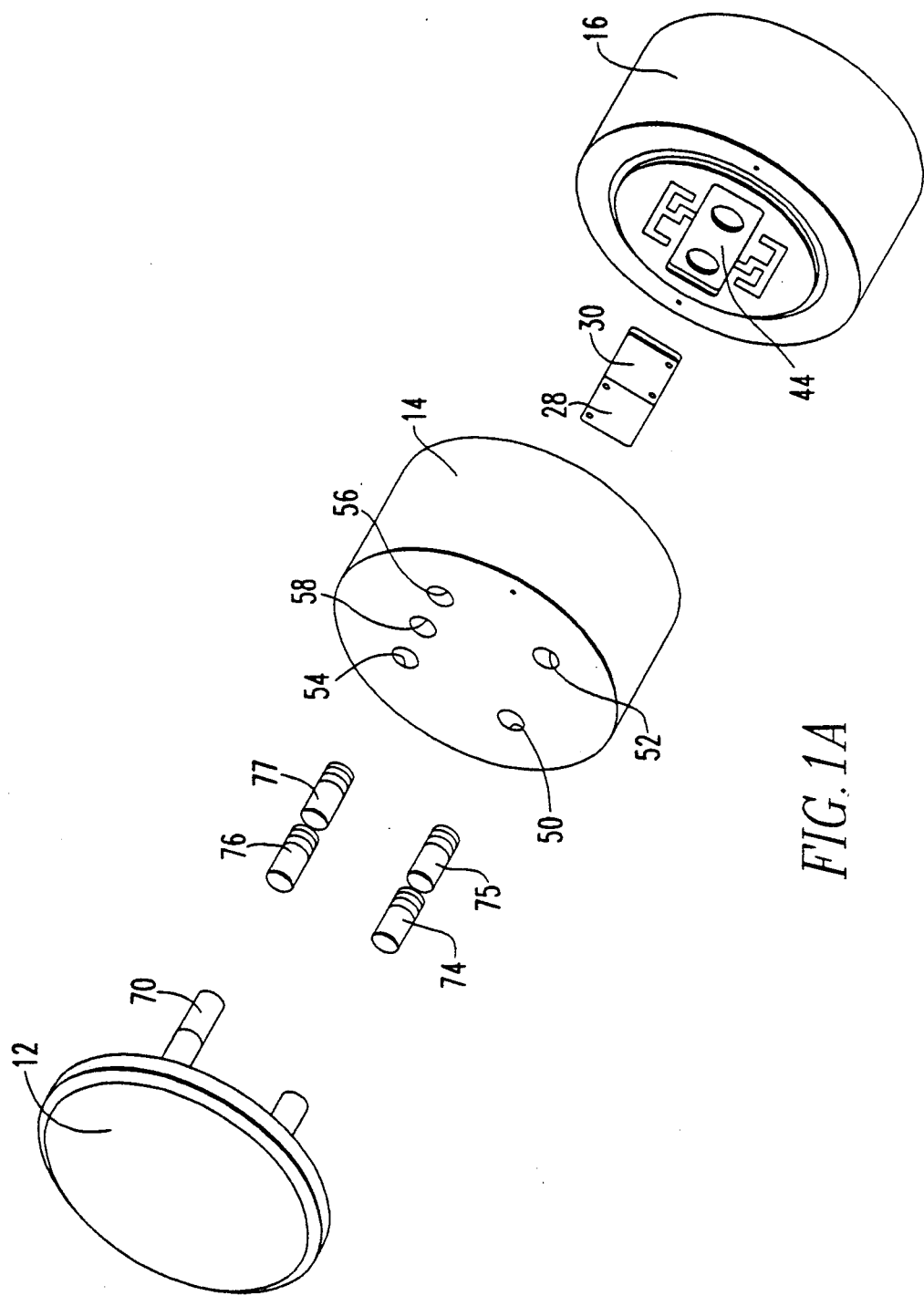
FIG. 1A is an exploded perspective view of the device of FIG. 1.

With reference to FIGS. 1A and 5, it can be seen that delivery elements 74 and 76 are disposed respectively in passageways 50 and 54. Similar delivery elements 75 and 77 are positioned in passageways 52 and 56. These elements are movable longitudinally of the corresponding passageway and may be in the form of a conventional actuator for a sealed hypodermic syringe. In this regard, a component of an agglutination reaction system is contained in each passageway between the delivery element and the corresponding capillary at the bottom end of each passageway. Thus, as can be seen viewing FIG. 5, the portions 50b and 54b of passageways 50 and 54 beneath elements 74 and 76 contain a component of an agglutination reaction system. Similarly passageways 52 an 56 have portions 52b and 56b beneath elements 75 and 77 which contain agglutination reaction system components.

Thus, with particular reference to FIGS. 1 and 13, when the plungers 62 through 68 of pusher assembly 12 are inserted into their respective passageways 50 through 56, the same will come into contact with the elements 74, 75, 76 and 77 and with continued movement of pusher assembly toward upper housing 14, the delivery elements will be moved toward conduits 46 and 48 so that the reaction system components are delivered into the conduit and on into the internal chambers 36 of the cells 28 and 30. And in this regard the agglutination reaction system, as will be described hereinafter, is a system where agglutination is either promoted or inhibited by the presence of a target analyte.

Distal end element 72 is formed from felt, foam, cotton or some other appropriate material which may or may not be pre-wetted prior to use. Element 72 is used to collect an unknown sample by immersing it in the sample or by simply moving it along a surface which is suspected of having been contaminated. As can be seen in FIG. 13, when the pusher assembly 12 is inserted into housing member 14, the sample collector is long enough so that the distal end element 72 is disposed in conduit 48. At the same time the plungers force the components of the agglutination reaction system from the corresponding passageways and into conduits 46 and 48 as the case may be. Since distal end 72 extends into conduit 48, when sample collector 70 is fully inserted into duct 58 the reaction components forced from passageways 54 and 56 by plungers 66 and 68 will wash past distal end element 72 so that analyte which is on distal end element 72 will be carried by the reaction system components into chamber 36 of cell 30. In this regard, it should be noted that the reaction system components from passageways 50 and 52 will not be contaminated with the unknown analyte so that the reaction components will simply flow into chamber 36 of cell 28 where they may react to provide a control system for comparison with the system in cell 30 which will contain the unknown.

Thus, the pusher member 12 with its plungers 62 through 68 and sample collector 70 and the corresponding passageways 50 through 56 and duct 58 present a delivery means for delivering an aqueous agglutination reaction system and an unknown substance containing target analyte to the cells 28 and 30.

As described above, an agglutination reaction will occur in each of the cells 28 and 30. The agglutination system in cell 30 will be effected by the presence of unknown analyte if it is present. Accordingly, as is well known to those of ordinary skill in the art to which the present invention pertains, the systems in cells 28 and 30 will agglutinate to a different extent if analyte is present in cell 30. On the other hand, if no analyte is detected, the agglutination in each cell will progress to the same extent. Thus, the cells may be examined to determine whether the extent of agglutination in one cell is different from the extent of agglutination in the other. This determination may be made utilizing the optical transmitting and receiving assembly 18.

Assembly 18 is inserted into lower housing member 16 as illustrated in FIG. 1. Thus, assembly 18 has a projecting end 78 configured to be received in socket 80 of lower housing member 16. Index marks may be provided to insure proper alignment with one optical transmitting and receiving unit aligned with cell 28 and with the other optical transmitting and receiving unit aligned with cell 30. To facilitate passage of light an opening 82 is provided beneath each cell as illustrated in FIG. 5. Each optical transmitting and receiving unit 20 and 22 has an optical transmitter 24 which projects light toward the corresponding cell in a direction transversely of the plane of chamber 36. Thus, light is projected in the direction of arrows 84 from optical transmitter 24 in FIG. 5. The light from transmitter 24 impinges on chamber 36 of the corresponding cell 28 or 30 and is reflected to an extent determined by the amount of agglutination which has occurred within chamber 36. Light is reflected in the direction of arrows 86 in FIG. 5 so that it impinges upon optical receiver 26 where the amount of light reflected can be measured. Thus, assembly 18 provides means for transmitting light in a first direction toward the reaction cell and detecting the intensity of light reflected from the cell. With reference to FIG. 5, a counter bore 88 is provided behind each cell 28 or 30 to provide an empty space to enhance reflection from the agglutinate by eliminating background.

The device 10 thus is an optical agglutination assay device. The device detects the presence of unknown analytes by comparing the amount of agglutination which occurs in a control cell with the amount of agglutination which occurs in an active cell affected by the presence of analyte. The preferred components of the agglutination reaction system are materials which react immunospecifically to cause agglutination to occur in the absence of the target analyte. In such system agglutination is inhibited whenever the target analyte is present.

Figure 11:
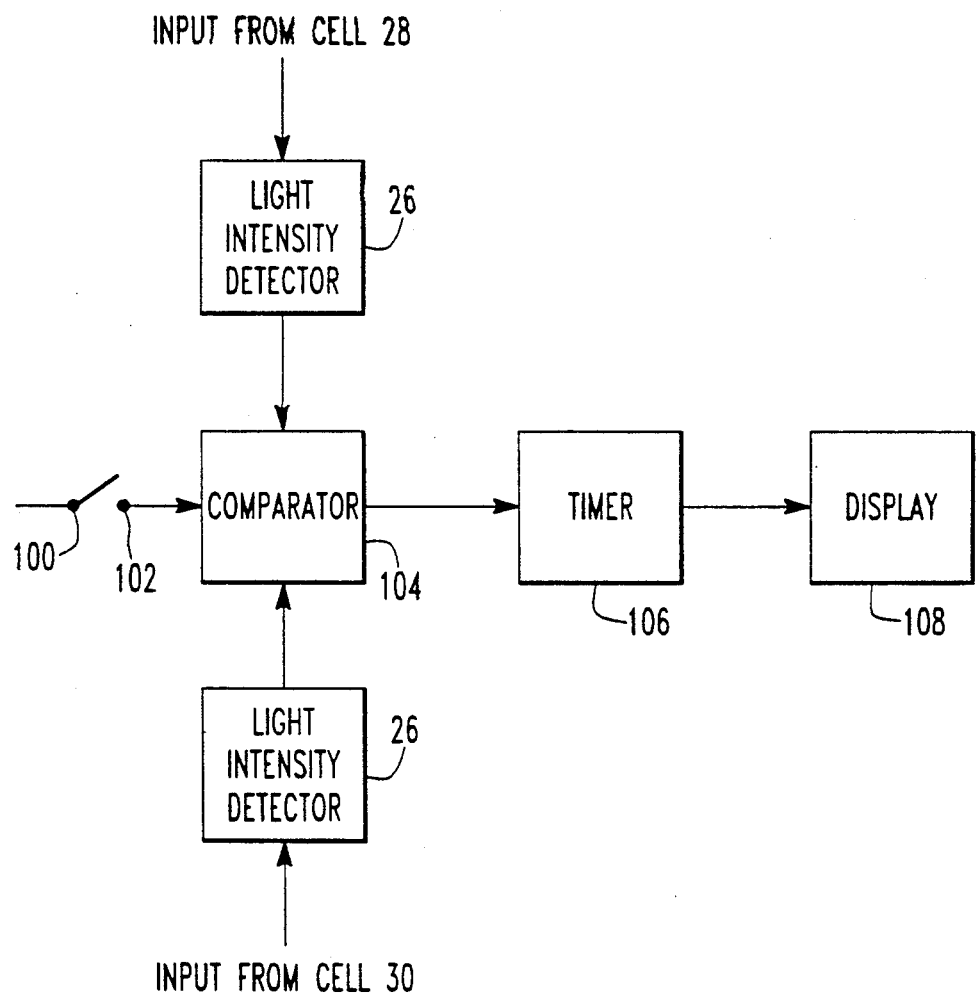
FIG. 11 is a schematic view of the electronics of the device.

Manifestly, as would be apparent to one of ordinary skill in the art to which the present invention pertains, the reaction should be allowed to incubate for a predetermined period of time before accurate measurements can be made. To facilitate this in the present device, switch contacts 100 and 102 may be provided on the pusher assembly 12 and the upper housing member 14 as illustrated in FIG. 1. Accordingly, when pusher assembly 12 is inserted into upper housing member 14 and pushed down far enough to activate the system (as in FIG. 13) the contacts 100 and 102 may be used to actuate a timing and measuring system as illustrated in FIG. 11. Thus, the input from optical transmitting and receiving unit 20 is compared with the input from optical transmitting and receiving unit 22 utilizing a comparator 104. Timer 106, which begins its timing cycle when contacts 100 and 102 are closed, operates to prevent a read out until the chemicals have had a sufficient period of time to incubate. After this period of time has elapsed timer 106 allows display 108 to read out the comparison being instantaneously made in the comparator 104. Of course, as would be appreciated by those of ordinary skill in the art, the comparator will need to be calibrated as a function of the particular system that is being evaluated in the unit. Such calibration is a well known and oft used procedure in this art.

The device 10 of the present invention may have great utility for detection of controlled drugs or materials such as explosives. In particular the device may be utilized to analyze for the presence of cocaine. A reaction environment is prepared in which the rate of an agglutination reaction is related in a smooth fashion to concentration over some useful range of a target analyte. The progress of the reaction is monitored using a light source and detector as described above. The intensity of the light measured with the photodetector at a specified time is a function of the analyte concentration. The cell 28, 30 provides a reaction chamber 36 which is approximately 10 mils thick, 500 mils wide and 500 mils long. The reaction cell is illuminated by a broad band near-infrared light source with a peak frequency intensity at approximately 0.8 micron ($\mu$). As described above, the reagents are introduced into the cell through a capillary tube.

The reagents consists of 1 $\mu$ uniform latex spheres onto which a hapten of the target analyte has been covalently bonded and a buffered solution containing a known concentration of an antibody to the target analyte. These reagents are added simultaneously by pusher assembly 12, briefly mixed, and introduced into the conduits 46 and 48 which are of capillary size to draw the reaction mixtures into the reaction cells. An agglutination reaction ensues in which the equilibrium point and the rate depends on the concentration of free analyte present in the sample solution. If no free analyte is present to compete with the latex bound hapten for antibody binding sites, agglutination occurs. When the target analyte is present, the analyte competes with the latex bound hapten for binding sites on the antibody and thus agglutination is inhibited. The infrared light source and photodetector monitor the reaction and, after a predetermined period of time, approximately 27 seconds, the intensity of the light signal at the photodetector is measured.

Figure 14:
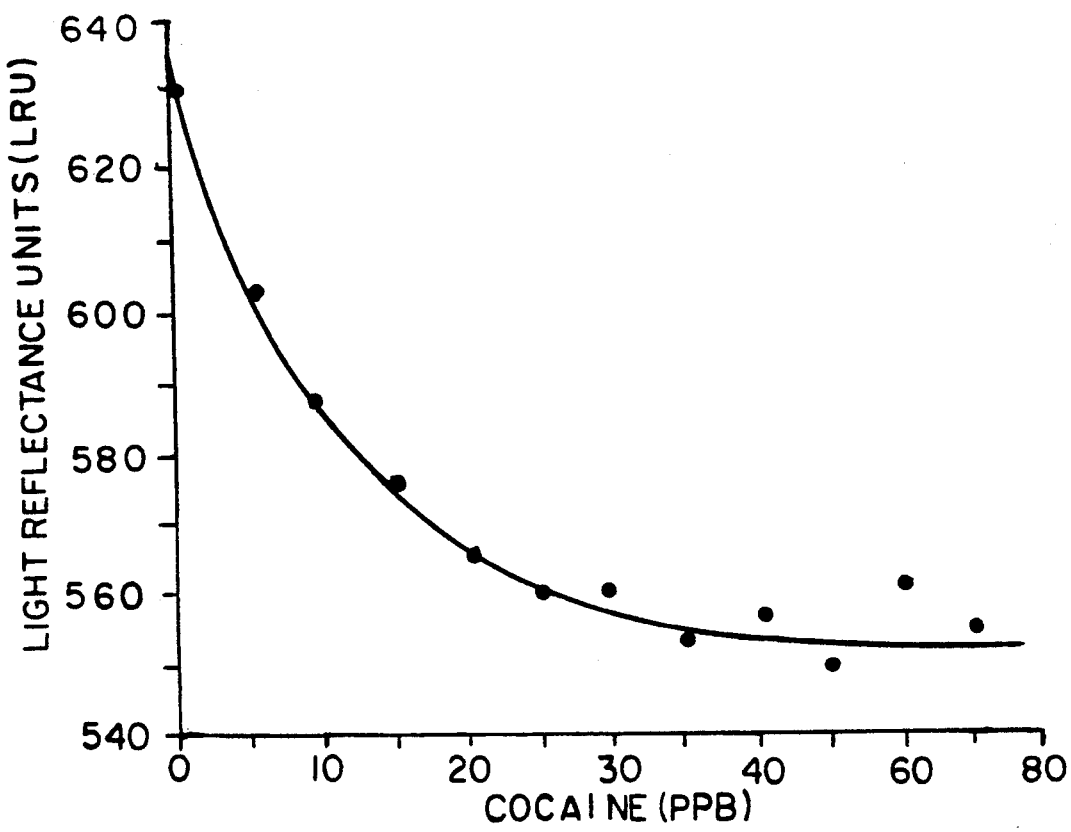
FIGS. 14, 15, 16 and 17 are graphs illustrating experiments conducted in accordance with the invention for detecting cocaine.
Figure 15:
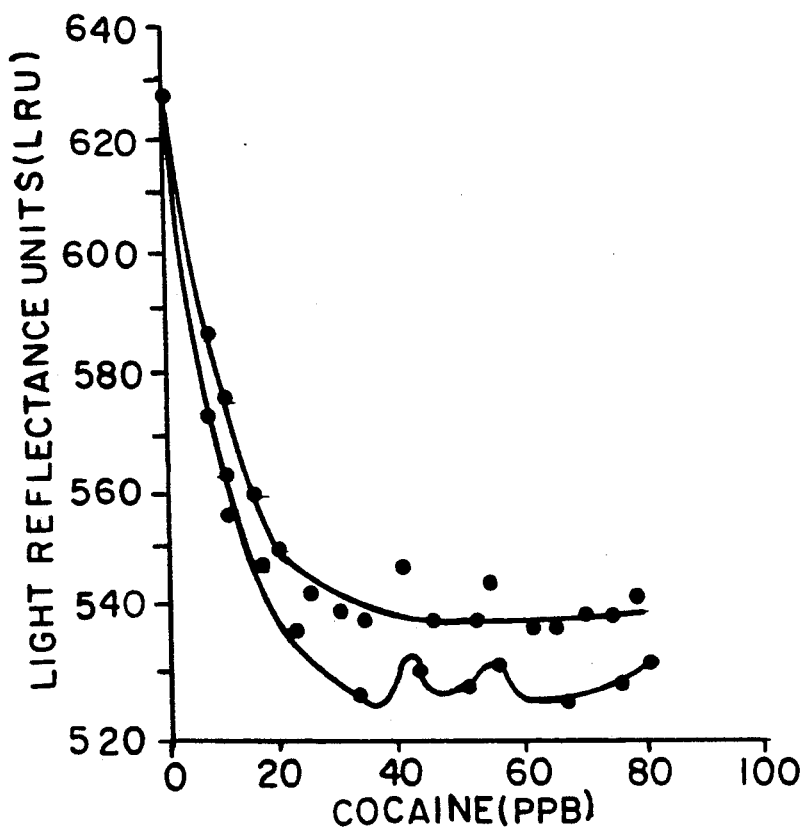
Figure 16:
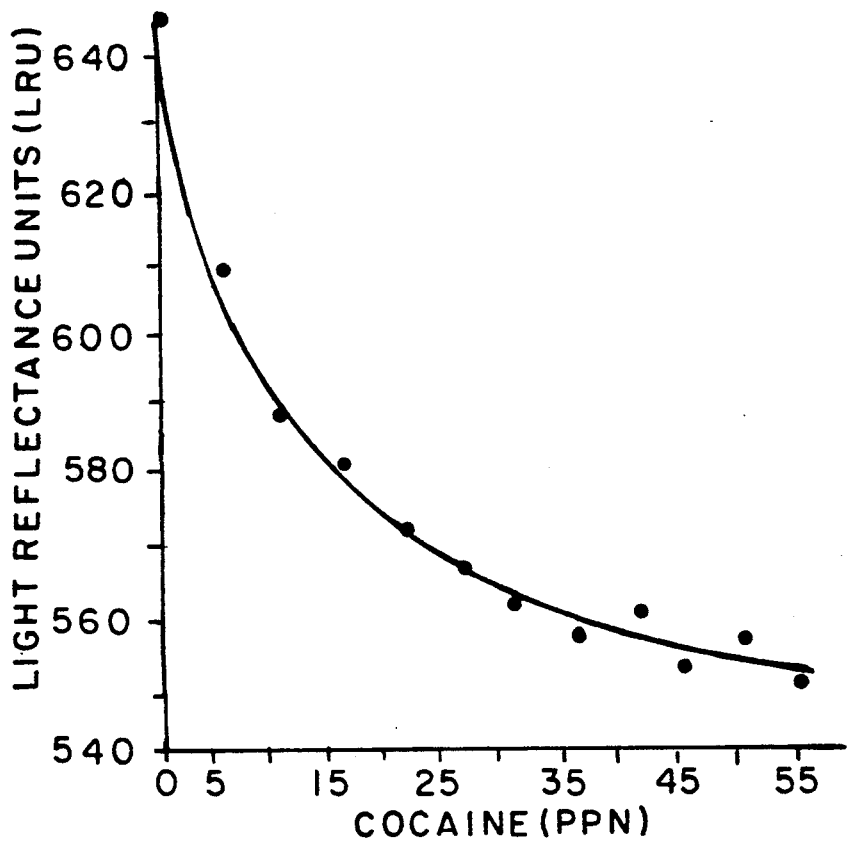

The device may be utilized to detect cocaine. FIGS. 14, 15 and 16 show the results of three trials of an experiment in which several solutions of a known concentration of cocaine analyte were reacted with fixed concentrations of cocaine coated with latex spheres and cocaine antibodies. These graphs show a smooth response curve for cocaine concentrations in a range of 0 to 40 parts per billion (ppb). In each case the photodetector measurement was made 3 minutes after the start of the reaction. The graph indicates that at cocaine concentrations above 40 ppb no agglutination was detectable.

Figure 17:
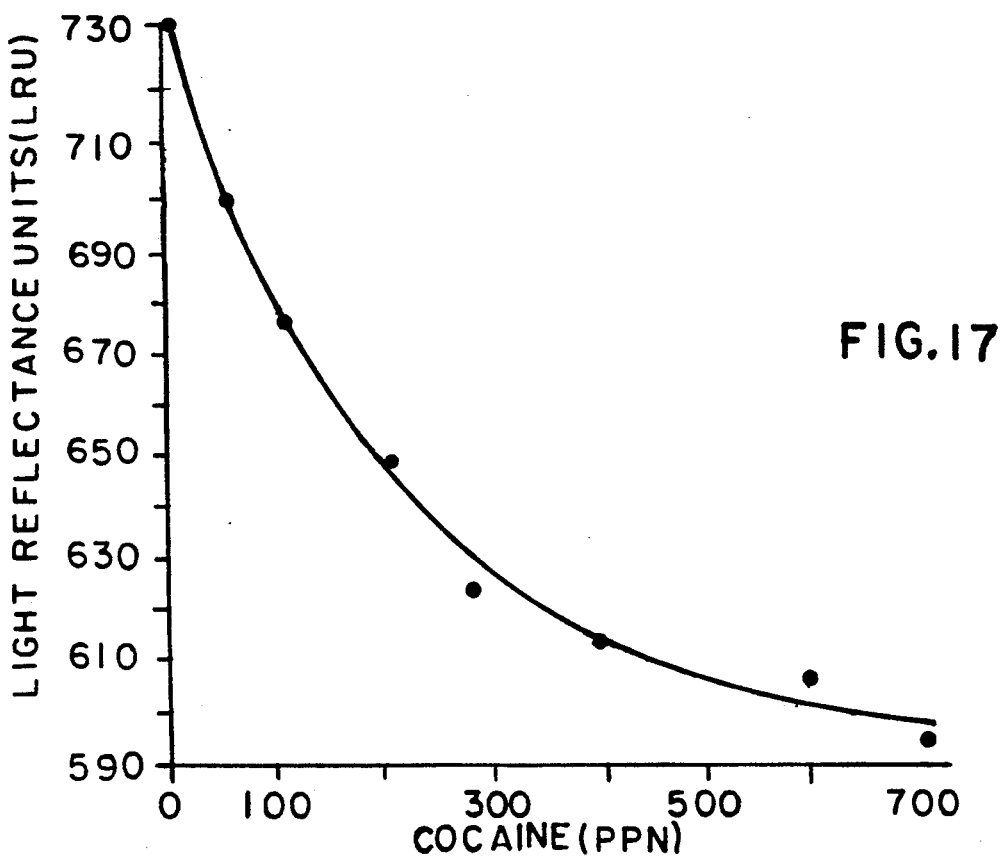

A second series of experiments was performed using a high concentration of cocaine antibodies. The results of these reactions are shown in FIG. 17. In this graph the shape of the response curve of the system is essentially the same as in the previous experiments. Of more importance, the decrease in the sensitivity from approximately 5.3 light reflectants units (LRU) per ppb cocaine in the first experiments to approximately 0.56 LRU/ppb in this series. Also the range of response has increased from 0 to 40 to 0 to 500 ppb. This may have practical implications in that it is believe that the background of certain analytes will be well above the 40 ppb limit of the earlier experiment and, although there may be other means to decrease the sensitivity of the system, the broader range reduces the potential for false positives or negatives in real situations and may allow the ability to discriminate high, medium, and low values as opposed to only yes or no determinations.

For use in connection with the device illustrated above, a commercially available cocaine agglutination reaction system may be utilized with appropriate sensitivity. The chemicals are available in the form of an ABUSCREEN ONTRAK test kit which is a commercial product (Order No. 42202) of Roche Diagnostic Systems. Thus, an antibody reagent consisting of mouse monoclonal anti-benzoylecgonine antibody in a buffered solution with 0.15% sodium azide as a preservative is one reactant, and the other reactant is a latex-benzoylecgonine conjugate in an aqueous solution with 0.15% sodium azide as preservative. In accordance with the present invention, one of these reagents is placed in passageway portions 50b and 54b and the other reagent is place in passageway portions 52b and 56b. The reagents will be mixed in conduits 46 or 48 as pusher 12 is actuated. If analyte is present on distal end 72, such analyte will be washed into chamber 36 of cell 30 by the reaction system components flowing through conduit 48.

Although the present device and system is based on the measurement of reflectance from a thin cell, it is also contemplated by and within the scope of the present invention that light transmission might also be measured as an indicator of the extent of agglutination in the reaction cell.

In accordance with the invention the two piece housing presented by housing members 14 and 16 may be pressure molded. These two components may thus be manufactured efficiently and economically to present a disposable housing. The pusher member 12 may also be formed by pressure molding techniques to facilitate disposability.

The device of the invention facilitates the collection of small samples, either wet, or dry, from a surface or container. The collector is designed for removability from the upper housing portion so that a sample can be collected and the pusher assembly reinserted into the housing. The action of reinserting the collection element initiates the release, mixing and subsequent reaction of all the reactants required to initiate one or more agglutination reactions. The progress of these reactions may be monitored and analyzed to detect or quantify one or more analytes collected on the collection surface.

The reaction cell assembly thus consists of one or more reaction cells with at least one wall that is transparent to the light used to monitor the cell, the reactants for conducting the assay and means for delivering the mixture into the appropriate reaction cell.

We claim:

1. An optical agglutination assay device comprising:
   a housing;
   a first separate, discrete hollow reaction cell mounted on said housing, said first cell defining a generally planar liquid receiving first reaction chamber having a thickness which facilitates the use of small quantities of reactants, does not interfere with the agglutination process, and is insufficient to substantially interfere with the passage of light through an aqueous reaction system in said first chamber along a first path of travel extending transversely of the plane of the first chamber;
   a second separate, discrete hollow reaction cell mounted on said housing, said second cell defining a generally planar liquid receiving second reaction chamber having a thickness which facilitates the use of small quantities of reactants, does not interfere with the agglutination process, and is insufficient to substantially interfere with the passage of light through an aqueous reaction system in said second chamber along a second path of travel extending transversely of the plane of the second chamber;
   first means for delivering an aqueous agglutination reaction system and an unknown substance suspected of containing a target analyte into said first chamber, said agglutination system being such that agglutination therein is promoted or inhibited in the presence of said analyte;
   second means for delivering an aqueous agglutination reaction system into said second chamber;
   means for transmitting light into said first chamber along said first path of travel;
   means for detecting the intensity of light reflected form said first chamber;
   means for transmitting light into said second chamber along said second path of travel;
   means for detecting the intensity of light reflected from said second chamber; and
   means for comparing the intensity of the light reflected from said first chamber with the intensity of the light reflected from said second chamber as a measure of the occurrence of agglutination in said first chamber, wherein said first delivering means comprises at least one first elongated passageway extending through said housing and arranged in liquid communication with said first chamber, and an elongated first plunger receivable in each said at least one first passageway for pushing components of a reaction system along said at least one first passageway and into said first chamber; said second delivering means comprising at least one second elongated passageway extending through said housing and arranged in liquid communication with said second chamber, and an elongated second plunger receivable in each said at least one second passageway for pushing components of a reaction system along said at least one second passageway and into said second chamber; said first delivering means further comprising an elongated sample duct extending through said housing and arranged in liquid communication with said first chamber, and an elongated sample collector receivable in said duct and configured to extend therethrough for positioning a sample in proximity to said first chamber.

2. An assay device as set forth in claim 1, wherein said first and second cells are positioned in side-by-side relationship with said first and second chambers disposed in essentially the same plane.

3. An assay device as set forth in claim 2, wherein said reaction system initially comprises two separate liquid mixtures and said first and second delivering means each comprises two of said elongated passageways extending through the housing and two of said elongated plungers.

4. An assay device as set for in claim 1, wherein said duct has an internal end and said at least one first passageway includes an internal conduit which communicates with said internal end and with said first chamber, said conduit being arranged so that reaction system components pushed by said first plunger flow past said internal end of the duct before entering said first chamber, said sample collector having a distal end element operable for carrying a sample and positioning the sample in fluids flowing through said conduit.

5. An assay device as set forth in claim 4, wherein said at least one first and second passageways and said duct are all disposed to extend in parallel through said housing, said first and second delivering means further including a common pusher member carrying said first and second plungers and said collector with the plungers and the collector mounted to extend in parallel and arranged so as to be respectively and simultaneously received in said at least one first and second passageways and said duct so that the plungers push said components at the same time that the collector positions the sample in said following fluids.

6. An assay device as set forth in claim 5, further comprising switch and timing means coupled with said pusher member for energizing said comparing means only after a preset incubation period.

7. An assay device as set for in claim 1, wherein said duct has an internal end and said first passageways each include an internal conduit which communicates with said internal end and with said first chamber, said conduits being arranged so that reaction system components pushed by said first plungers flow past said internal end of the duct before entering said first chamber, said sample collector having a distal end element operable for carrying a sample and positioning the sample in fluids flowing through said conduits.

8. An assay device as set forth in claim 7, wherein said first and second passageways and said duct are all disposed to extend in parallel through said housing, said first and second delivering means further including a common pusher member carrying said first and second plungers and said collector with the plungers and the collector mounted to extend in parallel and arranged so as to be respectively and simultaneously received in said first and second passageways and said duct so that the plungers push said components at the same time that the collector positions the sample in said flowing fluids.

9. An assay device as set forth in claim 8, further comprising switch and timing means coupled with said pusher member for energizing said comparing means only after a preset incubation period.

10. An optical agglutination assay device comprising:
a housing;
a separate, discrete hollow reaction cell removably mounted on said housing, said cell defining a generally planar liquid receiving reaction chamber having fixed dimensions including a thickness which facilitates the use of small quantities of reactants, does not interfere with the agglutination process and is insufficient to substantially interfere with the passage of light through an aqueous reaction system in said chamber along a path of travel which extends transversely of the plane of the chamber;
means for delivering an aqueous agglutination reaction system and an unknown substance suspected of containing a target analyte into said chamber, said agglutination system being such that agglutination therein is promoted or inhibited in the presence of said analyte;
means for transmitting light into said chamber along said path of travel; and
means for detecting the intensity of light reflected by or transmitted through said chamber as a measure of the occurrence of agglutination in said system, wherein said delivering means comprises at least one elongated passageway extending through said housing and arranged in liquid communication with said chamber, and an elongated plunger receivable in each said at least one passageway for pushing components of a reaction system along said at least one passageway and into said chamber, said delivering means further comprising an elongated sample duct extending through said housing and arranged in liquid communication with said chamber, and an elongated sample collector receivable in said duct and configured to extend therethrough for positioning a sample in proximity to said chamber.

11. An assay device as set forth in claim 10, wherein said reaction system initially comprises two separate liquid mixtures and said delivering means comprises two of said elongated passageways extending through the housing and two of said elongated plungers.

12. An assay device as set for in claim 10, wherein said duct has an internal end and said at least one passageway includes an internal conduit which communicates with said internal end of the duct and with said chamber, said conduit being arranged so that reaction system components pushed by said plunger flow past said internal end of the duct before entering said chamber, said sample collector having a distal end element operable for carrying a sample and positioning the sample in fluids flowing through said conduit.

13. An assay device as set forth in claim 12, wherein said at least one passageway and said duct are parallel and extend through said housing, said delivering means further including a pusher member carrying said plunger and said collector, said plunger and said collector being parallel and being mounted so as to be respectively and simultaneously received in said at least one passageway and said duct so that the plunger pushes said components at the same time that the collector positions the sample in said flowing fluids.

14. An assay device as set forth in claim 13, and switch further comprising timing means coupled with said pusher member for energizing said means for detecting intensity only after a preset incubation period.

15. An assay device as set for in claim 10, wherein said duct has an internal end and said passageways each include an internal conduit which communicates with said internal end of the duct and with said chamber, said conduits being arranged so that reaction system components pushed by said plungers flow past said internal end of the duct before entering said chamber, said sample collector having a distal end element operable for carrying a sample and positioning the sample in fluids flowing through said conduits.

16. An assay device as set forth in claim 15, wherein said passageways and said duct are disposed to extend in parallel through said housing, said delivering means further including a pusher member carrying said plungers and said collector with the plungers and the collector mounted to extend in parallel and arranged so as to be respectively and simultaneously received in said passageways and said duct so that the plungers push said components at the same time that the collector positions the sample in said flowing fluids.

17. An assay device as set forth in claim 16, further comprising switch and timing means coupled with said pusher member for energizing said means for detecting intensity only after a preset incubation period.

* * * * *